United States Patent
Nash

(10) Patent No.: US 9,717,718 B2
(45) Date of Patent: *Aug. 1, 2017

(54) ANTI-INFLAMMATORY COMPOUNDS

(71) Applicant: Phytoquest Limited, Aberystwyth (GB)

(72) Inventor: Robert James Nash, Ystrad-Meurig (GB)

(73) Assignee: Phytoquest Limited, Aberystwyth (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/086,796

(22) Filed: Mar. 31, 2016

(65) Prior Publication Data

US 2016/0317513 A1    Nov. 3, 2016

Related U.S. Application Data

(63) Continuation of application No. 14/251,074, filed on Apr. 11, 2014, now Pat. No. 9,326,977, which is a continuation of application No. PCT/GB2012/000768, filed on Oct. 10, 2012.

(30) Foreign Application Priority Data

Oct. 11, 2011 (GB) .................................. 1117490.1

(51) Int. Cl.

| | |
|---|---|
| *A61K 31/445* | (2006.01) |
| *A61K 36/42* | (2006.01) |
| *C07D 211/60* | (2006.01) |
| *A61K 8/49* | (2006.01) |
| *A61Q 19/00* | (2006.01) |
| *A61K 45/06* | (2006.01) |
| *A61Q 19/10* | (2006.01) |
| *G01N 33/94* | (2006.01) |
| *A23L 33/105* | (2016.01) |
| *A61K 9/00* | (2006.01) |

(52) U.S. Cl.

CPC .......... *A61K 31/445* (2013.01); *A23L 33/105* (2016.08); *A61K 8/4926* (2013.01); *A61K 9/006* (2013.01); *A61K 9/0014* (2013.01); *A61K 9/0053* (2013.01); *A61K 36/42* (2013.01); *A61K 45/06* (2013.01); *A61Q 19/00* (2013.01); *A61Q 19/10* (2013.01); *C07D 211/60* (2013.01); *G01N 33/94* (2013.01); *Y10T 436/145555* (2015.01)

(58) Field of Classification Search

CPC ..................................................... A61K 31/445

USPC ......................................................... 514/315

See application file for complete search history.

(56) References Cited

U.S. PATENT DOCUMENTS

| 6,927,294 B1 | 8/2005 | Petasis et al. |
| 9,326,977 B2 | 5/2016 | Nash |

FOREIGN PATENT DOCUMENTS

| DE | 36 28 486 A1 | 2/1988 |
| WO | WO 2009/103953 A1 | 8/2009 |
| WO | WO 2013/054070 A1 | 4/2013 |

OTHER PUBLICATIONS

International Search Report and Written Opinion mailed Feb. 18, 2013 for Application No. PCT/GB2012/000768.
International Preliminary Report on Patentability mailed Apr. 24, 2014 in connection with PCT/GB2012/000768.
Bashyal et al., Enantiospecific Syntheses of 2S,3R,4R,5S-Trihydroxypipecolic Acid, 2R,3R,4R,5S-Trihydroxypipecolic Acid, 2S,4S,5S-Dihydroxypipecolic Acid, and Bulgecinine from D-Glucuronolactone. Tetrahedron Lett. 1986;27(27):3205-8.
Englebienne, Effects of introducing silicon isosteres in COX-2 inhibitors: a preliminary in silico evaluation. Med Chem. May 2005;1(3):215-26.
Kushner et al., Pharmacological uses and perspectives of heavy water and deuterated compounds. Can J Physiol Pharmacol. Feb. 1999;77(2):79-88.
Nash et al., Endometrial explant culture for characterizing equine endometritis. Am J Reprod Immunol. Feb. 2008;59(2):105-17. doi: 10.1111/j.1600-0897.2007.00548.x.
Tacke et al., Sila-substitution—a useful strategy for drug design? Endeavour. 1986;10(4):191-7.
Watson et al., Glycosidase-inhibiting pyrrolidine alkaloids from Hyacinthoide non-scripta. Phytochemistry. Sep. 1997;46(2):255-9.
Watson et al., Polyhydroxylated alkaloids—natural occurrence and therapeutic applications. Phytochemistry. Feb. 2001;56(3):265-95.

*Primary Examiner* — Raymond Henley, III
(74) *Attorney, Agent, or Firm* — Wolf, Greenfield & Sacks, P.C.

(57) ABSTRACT

Compositions comprising isolated ido-BR1 are described for use in therapy or prophylaxis, including the treatment of inflammatory diseases (for example as anti-inflammatory drugs) and to reduce inflammation. Also described are methods for monitoring the quality of a Cucurbitaceae extract, to processes for producing a Cucurbitaceae extract as well as to Cucurbitaceae extracts obtainable by such processes.

20 Claims, No Drawings

ANTI-INFLAMMATORY COMPOUNDS

RELATED APPLICATIONS

This application is a continuation of and claims the benefit under 35 U.S.C. §120 to U.S. Application, U.S. Ser. No. 14/251,074, filed Apr. 11, 2014, now U.S. Pat. No. 9,326,977, which is a continuation of International Patent Application Serial No. PCT/GB2012/000768, filed Oct. 10, 2012, the entire contents of which are incorporated herein by reference. Foreign priority benefits are claimed under 35 U.S.C. §119(a)-(d) or 35 U.S.C. §365(b) of British application number 1117490.1, filed Oct. 11, 2011, the entire contents of which are incorporated herein by reference.

FIELD OF THE INVENTION

This invention relates to certain iminosugar acids for treating inflammatory disease (for example as anti-inflammatory drugs) and to reduce inflammation. The invention therefore finds application in methods for the treatment of inflammatory diseases and for reducing inflammation.

The invention also relates to methods for monitoring the quality of a Cucurbitaceae extract, to processes for producing a Cucurbitaceae extract as well as to Cucurbitaceae extracts obtainable by such processes.

BACKGROUND OF THE INVENTION

The cucumber (*Cucumis sativus*) is a widely cultivated plant in the gourd family Cucurbitaceae, which includes squash. Cucumbers originated in India and have been cultivated for at least 3000 years in Western Asia, and probably introduced to other parts of Europe by the Romans. Records of cucumber cultivation appear in France in the 9th century, England in the 14th century, and in North America by the mid-16th century.

Cucumbers and cucumber extracts have long been recognized as having anti-inflammatory properties, and have been used topically for various types of skin problems, including swelling under the eyes and sunburn. Cucumber was very popular in the ancient civilizations of Egypt, Greece and Rome, where it was used not only as a food but also for its skin healing properties.

However, the active component(s) have not been reported.

It has now been discovered that the iminosugar acid ido-BR1 occurs in older cucumber varieties but is absent in certain modern commercial varieties. It has been shown to be a major component of certain cucumber fruits, certain squashes and gourds and is the only iminosugar acid in cucumber.

Iminosugar acids (ISAs) constitute a subclass of the more widely distributed class of phytochemicals known as iminosugars. Many known ISAs are phytochemicals, present as secondary metabolites in plant tissues (where they may play a role in defence). While iminosugars are widely distributed in plants (Watson et al. (2001) Phytochemistry 56: 265-2951), the iminosugar acids are much less widely distributed.

Thus, the discovery that the botanical distribution of the iminosugar acid ido-BR1 correlates with medicinal plants used for the treatment of inflammatory disease is of great significance.

The synthesis of ido-BR1 has been described in Fleet et al. (1986) Tetrahedron Lett. 27: 3205-3208.

SUMMARY OF THE INVENTION

The present invention is based, at least in part, on the surprising discovery that the botanical distribution of ido-BR1 correlates with medicinal plants used for the treatment of inflammatory diseases. Thus, for the first time ido-BR1 has been identified as an important bioactive principle in established anti-inflammatory herbal medicines.

Thus, according to the invention there is provided (2R,3R,4R,5S)-3,4,5-trihydroxypiperidine-2-carboxylic acid (6-epiBR1; 2R,3R,4R,5S-Trihydroxypipecolic acid; ido-BR1) for use in therapy or prophylaxis.

Other aspects and preferred embodiments of the invention are defined and described in the claims set out below.

As used herein, the term ido-BR1 is intended to define sensu stricto a compound of the formula:

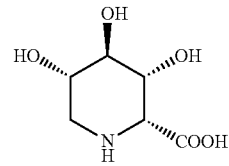

but is also to be interpreted sensu lato to include pharmaceutically acceptable salts, solvates, metabolites, prodrugs, bioisosteres, derivatives and protected forms thereof.

Those skilled in the art will appreciate that various N-substituted derivatives of ido-BR1 are likely to share its anti-inflammatory properties, and so the pharmaceutically acceptable derivatives contemplated specifically include compounds of the formula:

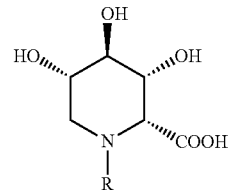

in which R represents optionally substituted $C_{1-15}$ alkyl, $C_{1-15}$ alkenyl or $C_{1-15}$ alkynyl.

DETAILED DESCRIPTION OF THE INVENTION

All publications, patents, patent applications and other references mentioned herein are hereby incorporated by reference in their entireties for all purposes as if each individual publication, patent or patent application were specifically and individually indicated to be incorporated by reference and the content thereof recited in full.

DEFINITIONS

Where used herein and unless specifically indicated otherwise, the following terms are intended to have the following meanings in addition to any broader (or narrower) meanings the terms might enjoy in the art:

Unless otherwise required by context, the use herein of the singular is to be read to include the plural and vice versa. The term "a" or "an" used in relation to an entity is to be read to refer to one or more of that entity. As such, the terms "a" (or "an"), "one or more," and "at least one" are used interchangeably herein.

As used herein, the term "comprise," or variations thereof such as "comprises" or "comprising," are to be read to indicate the inclusion of any recited integer (e.g. a feature, element, characteristic, property, method/process step or limitation) or group of integers (e.g. features, element, characteristics, properties, method/process steps or limitations) but not the exclusion of any other integer or group of integers. Thus, as used herein the term "comprising" is inclusive or open-ended and does not exclude additional, unrecited integers or method/process steps.

The phrase "consisting essentially of" is used herein to require the specified integer(s) or steps as well as those which do not materially affect the character or function of the claimed invention.

As used herein, the term "consisting" is used to indicate the presence of the recited integer (e.g. a feature, element, characteristic, property, method/process step or limitation) or group of integers (e.g. features, element, characteristics, properties, method/process steps or limitations) alone.

As used herein, the term "disease" is used to define any abnormal condition that impairs physiological function and is associated with specific symptoms. The term is used broadly to encompass any disorder, illness, abnormality, pathology, sickness, condition or syndrome in which physiological function is impaired irrespective of the nature of the aetiology (or indeed whether the aetiological basis for the disease is established). It therefore encompasses conditions arising from infection, trauma, injury, surgery, radiological ablation, poisoning or nutritional deficiencies.

As used herein, the term "treatment" or "treating" refers to an intervention (e.g. the administration of an agent to a subject) which cures, ameliorates or lessens the symptoms of a disease or removes (or lessens the impact of) its cause(s) (for example, pathological variegated states). In this case, the term is used synonymously with the term "therapy".

Additionally, the terms "treatment" or "treating" refers to an intervention (e.g. the administration of an agent to a subject) which prevents or delays the onset or progression of a disease or reduces (or eradicates) its incidence within a treated population. In this case, the term treatment is used synonymously with the term "prophylaxis".

The term "subject" (which is to be read to include "individual", "animal", "patient" or "mammal" where context permits) defines any subject, particularly a mammalian subject, for whom treatment is indicated. Mammalian subjects include, but are not limited to, humans, domestic animals, farm animals, zoo animals, sport animals and pet animals. In preferred embodiments, the subject is a human.

As used herein, an effective amount of a compound or composition defines an amount that can be administered to a subject without excessive toxicity, irritation, allergic response, or other problem or complication, commensurate with a reasonable benefit/risk ratio, but one that is sufficient to provide the desired effect, e.g. the treatment or prophylaxis manifested by a permanent or temporary improvement in the subjects condition. The amount will vary from subject to subject, depending on the age and general condition of the individual, mode of administration and other factors. Thus, while it is not possible to specify an exact effective amount, those skilled in the art will be able to determine an appropriate "effective" amount in any individual case using routine experimentation and background general knowledge. A therapeutic result in this context includes eradication or lessening of symptoms, reduced pain or discomfort, prolonged survival, improved mobility and other markers of clinical improvement. A therapeutic result need not be a complete cure.

As used herein, the term "combination", as applied to two or more compounds and/or agents (also referred to herein as the components), is intended to define material in which the two or more compounds/agents are associated. The terms "combined" and "combining" in this context are to be interpreted accordingly.

The association of the two or more compounds/agents in a combination may be physical or non-physical. Examples of physically associated combined compounds/agents include:

compositions (e.g. unitary formulations) comprising the two or more compounds/agents in admixture (for example within the same unit dose);

compositions comprising material in which the two or more compounds/agents are chemically/physicochemically linked (for example by crosslinking, molecular agglomeration or binding to a common vehicle moiety);

compositions comprising material in which the two or more compounds/agents are chemically/physicochemically co-packaged (for example, disposed on or within lipid vesicles, particles (e.g. micro- or nanoparticles) or emulsion droplets);

pharmaceutical kits, pharmaceutical packs or patient packs in which the two or more compounds/agents are co-packaged or co-presented (e.g. as part of an array of unit doses);

Examples of non-physically associated combined compounds/agents include:

material (e.g. a non-unitary formulation) comprising at least one of the two or more compounds/agents together with instructions for the extemporaneous association of the at least one compound/agent to form a physical association of the two or more compounds/agents;

material (e.g. a non-unitary formulation) comprising at least one of the two or more compounds/agents together with instructions for combination therapy with the two or more compounds/agents;

material comprising at least one of the two or more compounds/agents together with instructions for administration to a patient population in which the other(s) of the two or more compounds/agents have been (or are being) administered;

material comprising at least one of the two or more compounds/agents in an amount or in a form which is specifically adapted for use in combination with the other(s) of the two or more compounds/agents.

As used herein, the term "combination therapy" is intended to define therapies which comprise the use of a combination of two or more compounds/agents (as defined above). Thus, references to "combination therapy", "combinations" and the use of compounds/agents "in combination" in this application may refer to compounds/agents that are administered as part of the same overall treatment regimen. As such, the posology of each of the two or more compounds/agents may differ: each may be administered at the same time or at different times. It will therefore be appreciated that the compounds/agents of the combination may be administered sequentially (e.g. before or after) or simultaneously, either in the same pharmaceutical formulation (i.e. together), or in different pharmaceutical formulations (i.e. separately). Simultaneously in the same formulation is as a unitary formulation whereas simultaneously in different pharmaceutical formulations is non-unitary. The posologies of each of the two or more compounds/agents in a combination therapy may also differ with respect to the route of administration.

As used herein, the term "pharmaceutical kit" defines an array of one or more unit doses of a pharmaceutical composition together with dosing means (e.g. measuring device) and/or delivery means (e.g. inhaler or syringe), optionally all contained within common outer packaging. In pharmaceutical kits comprising a combination of two or more compounds/agents, the individual compounds/agents may unitary or non-unitary formulations. The unit dose(s) may be contained within a blister pack. The pharmaceutical kit may optionally further comprise instructions for use.

As used herein, the term "pharmaceutical pack" defines an array of one or more unit doses of a pharmaceutical composition, optionally contained within common outer packaging. In pharmaceutical packs comprising a combination of two or more compounds/agents, the individual compounds/agents may unitary or non-unitary formulations. The unit dose(s) may be contained within a blister pack. The pharmaceutical pack may optionally further comprise instructions for use.

As used herein, the term "patient pack" defines a package, prescribed to a patient, which contains pharmaceutical compositions for the whole course of treatment. Patient packs usually contain one or more blister pack(s). Patient packs have an advantage over traditional prescriptions, where a pharmacist divides a patient's supply of a pharmaceutical from a bulk supply, in that the patient always has access to the package insert contained in the patient pack, normally missing in patient prescriptions. The inclusion of a package insert has been shown to improve patient compliance with the physician's instructions.

The combinations of the invention may produce a therapeutically efficacious effect relative to the therapeutic effect of the individual compounds/agents when administered separately.

The term bioisostere (or simply isostere) is a term of art used to define drug analogues in which one or more atoms (or groups of atoms) have been substituted with replacement atoms (or groups of atoms) having similar steric and/or electronic features to those atoms which they replace. The substitution of a hydrogen atom or a hydroxyl group with a fluorine atom is a commonly employed bioisosteric replacement. Sila-substitution (C/Si-exchange) is a relatively recent technique for producing isosteres. This approach involves the replacement of one or more specific carbon atoms in a compound with silicon (for a review, see Tacke and Zilch (1986) Endeavour, New Series 10: 191-197). The sila-substituted isosteres (silicon isosteres) may exhibit improved pharmacological properties, and may for example be better tolerated, have a longer half-life or exhibit increased potency (see for example Englebienne (2005) Med. Chem., 1(3): 215-226). Similarly, replacement of an atom by one of its isotopes, for example hydrogen by deuterium, may also lead to improved pharmacological properties, for example leading to longer half-life (see for example Kushner et al (1999) Can J Physiol Pharmacol. 77(2):79-88). In its broadest aspect, the present invention contemplates all bioisosteres (and specifically, all silicon bioisosteres) of the compounds of the invention.

The terms derivative and pharmaceutically acceptable derivative as applied to the compounds of the invention define compounds which are obtained (or obtainable) by chemical derivatization of the parent compound of the invention. The pharmaceutically acceptable derivatives are therefore suitable for administration to or use in contact with the tissues of humans without undue toxicity, irritation or allergic response (i.e. commensurate with a reasonable benefit/risk ratio). Preferred derivatives are those obtained (or obtainable) by alkylation, esterification or acylation of the parent compounds. Thus, the pharmaceutically acceptable derivates of the compound of the invention includes N-oxides and esters thereof.

The pharmaceutically acceptable derivatives of the invention may retain some or all of the biological activities described herein. In some cases, the biological activity is increased by derivatization. The derivatives may act as pro-drugs, and one or more of the biological activities described herein may arise only after in vivo processing. Particularly preferred pro-drugs are ester derivatives which are esterified at one or more of the free hydroxyls and which are activated by hydrolysis in vivo. Derivatization may also augment other biological activities of the compound, for example bioavailability and/or glycosidase inhibitory profile. For example, derivatization may increase CNS penetration (e.g. penetration of the blood-brain barrier).

The term pharmaceutically acceptable salt defines any non-toxic organic or inorganic acid addition salt of the free base which are suitable for use in contact with the tissues of humans and lower animals without undue toxicity, irritation, allergic response and which are commensurate with a reasonable benefit/risk ratio. Suitable pharmaceutically acceptable salts are well known in the art. Examples are the salts with inorganic acids (for example hydrochloric, hydrobromic, sulphuric and phosphoric acids), organic carboxylic acids (for example acetic, propionic, glycolic, lactic, pyruvic, malonic, succinic, fumaric, malic, tartaric, citric, ascorbic, maleic, hydroxymaleic, dihydroxymaleic, benzoic, phenylacetic, 4-aminobenzoic, 4-hydroxybenzoic, anthranilic, cinnamic, salicylic, 2-phenoxybenzoic, 2-acetoxybenzoic and mandelic acid) and organic sulfonic acids (for example methanesulfonic acid and p-toluenesulfonic acid).

These salts and the free base compounds can exist in either a hydrated or a substantially anhydrous form. Crystalline forms, including all polymorphic forms, of the iminosugars of the invention are also contemplated and in general the acid addition salts of the compounds are crystalline materials which are soluble in water and various hydrophilic organic solvents and which in comparison to their free base forms, demonstrate higher melting points and an increased solubility.

The term pharmaceutically acceptable metabolite as applied to the compounds of the invention defines a pharmacologically active product produced through metabolism in the body of the specified compound or salt thereof.

The term pharmaceutically acceptable prodrug as applied to the compounds of the invention defines any pharmaceutically acceptable compound that may be converted under physiological conditions or by solvolysis to the specified compound, to a pharmaceutically acceptable salt of such compound or to a compound that shares at least some of the activity of the specified compound.

Prodrugs and active metabolites of the compounds of the invention may be identified using routine techniques known in the art (see for example, Bertolini et al., J. Med. Chem., 1997, 40, 2011-2016).

In the present specification the term "alkyl" defines a straight or branched saturated hydrocarbon chain. The term "$C_1$-$C_6$ alkyl" refers to a straight or branched saturated hydrocarbon chain having one to six carbon atoms. The term "$C_1$-$C_9$ alkyl" refers to a straight or branched saturated hydrocarbon chain having one to nine carbon atoms. The term "$C_1$-$C_{15}$ alkyl" refers to a straight or branched saturated hydrocarbon chain having one to fifteen carbon atoms. Preferred is $C_1$-$C_6$ alkyl. Examples include methyl, ethyl, n-propyl, isopropyl, t-butyl, n-hexyl. The alkyl groups of the invention may be optionally substituted by one or more halogen atoms.

In the present specification the term "alkenyl" defines a straight or branched hydrocarbon chain having containing at least one carbon-carbon double bond. The term "$C_1$-$C_6$ alkenyl" refers to a straight or branched unsaturated hydrocarbon chain having one to six carbon atoms. The term "$C_1$-$C_9$ alkenyl" refers to a straight or branched unsaturated hydrocarbon chain having one to nine carbon atoms. The term "$C_1$-$C_{15}$ alkenyl" refers to a straight or branched unsaturated hydrocarbon chain having one to fifteen carbon atoms. Preferred is $C_1$-$C_6$ alkenyl. Examples include ethenyl, 2-propenyl, and 3-hexenyl. The alkenyl groups of the invention may be optionally substituted by one or more halogen atoms.

In the present specification the term "alkynyl" defines a straight or branched hydrocarbon chain having containing at least one carbon-carbon triple bond. The term "$C_1$-$C_6$ alkynyl" refers to a straight or branched unsaturated hydrocarbon chain having one to six carbon atoms. The term "$C_1$-$C_9$ alkynyl" refers to a straight or branched unsaturated hydrocarbon chain having one to nine carbon atoms. The term "$C_1$-$C_{15}$ alkynyl" refers to a straight or branched unsaturated hydrocarbon chain having one to fifteen carbon atoms. Preferred is $C_1$-$C_6$ alkynyl. Examples include ethynyl, 2-propynyl, and 3-hexynyl. The alkynyl groups of the invention may be optionally substituted by one or more halogen atoms.

The term isolated as applied to the ido-BR1 of the invention is used herein to indicate that the ido-BR1 exists in a physical milieu distinct from that in which it occurs in nature (or in the case of synthetic ido-BR1, is purified to some degree). For example, the isolated ido-BR1 may be substantially isolated (for example purified) with respect to the complex cellular milieu in which it naturally occurs (or with respect to the some or all of the starting products, intermediates, buffers, solvents, reactants and/or co-products from which it is synthesised).

When the isolated material (e.g. synthetic, non-naturally occurring ido-BR1) is purified, the absolute level of purity is not critical and those skilled in the art can readily determine appropriate levels of purity according to the use to which the material is to be put. Preferred, however, are purity levels of 50% w/w, 60% w/w, 70% w/w, 80% w/w, 90% w/w, 99% w/w or higher. In some circumstances, the isolated ido-BR1 forms part of a composition (for example a more or less crude extract containing many other substances) or buffer system, which may for example contain other components. In other circumstances, the isolated ido-BR1 may be purified to essential homogeneity, for example as determined spectrophotometrically, by NMR or by chromatography (for example GC-MS of the trimethylsilyl-derivatives).

The term herbal medicine is used herein to define a pharmaceutical composition in which at least one active principle (e.g. the ido-BR1) is not chemically synthesized and is a phytochemical constituent of a plant. In most cases, this non-synthetic active principle is not isolated (as defined herein), but present together with other phytochemicals with which it is associated in the source plant. In some cases, however, the plant-derived bioactive principle(s) may be in a concentrated fraction or isolated (sometimes involving high degrees of purification). In many cases, however, the herbal medicine comprises a more or less crude extract, infusion or fraction of a plant or even an unprocessed whole plant (or part thereof), though in such cases the plant (or plant part) is usually at least dried and/or milled.

The term nutraceutical is used herein to define a food product (or isolate thereof) which provides physiological benefits or protects against disease. Preferred nutraceuticals of the invention are anti-inflammatory.

The term standard specification is used herein to define a characteristic, or a phytochemical profile, which is correlated with an acceptable quality of the herbal medicine, cosmetic or nutraceutical. In this context, the term quality is used to define the overall fitness of the product for its intended use, and includes the presence of ido-BR1 at an appropriate concentration.

Posology

The compounds of the present invention can be administered topically or by oral or parenteral routes, including intravenous, intramuscular, intraperitoneal, subcutaneous, transdermal, airway (aerosol), rectal, vaginal and topical (including buccal and sublingual) administration.

The amount administered can vary widely according to the particular dosage unit employed, the period of treatment, the age and sex of the patient treated, the nature and extent of the disorder treated, and the particular compound selected.

Moreover, the compounds of the invention can be used in conjunction with other agents known to be useful in the treatment of diseases or disorders arising from protein folding abnormalities (as described infra) and in such embodiments the dose may be adjusted accordingly.

In general, the effective amount of the compound administered will generally range from about 0.01 mg/kg to 500 mg/kg daily. A unit dosage may contain from 0.05 to 500 mg of the compound, and can be taken one or more times per day. The compound can be administered with a pharmaceutical carrier using conventional dosage unit forms either orally, parenterally, or topically, as described below.

The preferred route of administration is oral administration. In general a suitable dose will be in the range of 0.01 to 500 mg per kilogram body weight of the recipient per day, preferably in the range of 0.1 to 50 mg per kilogram body weight per day and most preferably in the range 1 to 5 mg per kilogram body weight per day.

The desired dose is preferably presented as a single dose for daily administration. However, two, three, four, five or six or more sub-doses administered at appropriate intervals throughout the day may also be employed. These sub-doses may be administered in unit dosage forms, for example, containing 0.001 to 100 mg, preferably 0.01 to 10 mg, and most preferably 0.5 to 1.0 mg of active ingredient per unit dosage form.

Formulation

The compound for use according to the invention may take any form. It may be synthetic or isolated from natural sources (for example from any of the botanical sources identified herein, including for example a botanical source selected from plants of the family Cucurbitaceae (for example, plants of the genus Cucumis, e.g. plants of the species Cucumis sativus). Particularly preferred as botanical source are fruits of the foregoing plants, for example cucumbers, pumpkins, squashes or gourds.

When isolated from a natural source, the ido-BR1 may be purified. However, the compositions of the invention may take the form of herbal medicines, as hereinbefore defined. Such herbal medicines preferably are analysed to determine whether they meet a standard specification prior to use.

The herbal medicines for use according to the invention may be dried plant material. Alternatively, the herbal medicine may be processed plant material, the processing involving physical or chemical pre-processing, for example powdering, grinding, freezing, evaporation, filtration, pressing, spray drying, extrusion, supercritical solvent extraction and tincture production. In cases where the herbal medicine is administered or sold in the form of a whole plant (or part thereof), the plant material may be dried prior to use. Any convenient form of drying may be used, including freeze-drying, spray drying or air-drying.

Ido-BR1 may be separated from the higher molecular weight components such as proteins and polysaccharides by using various membrane technologies. These include microfiltration, ultrafiltration and nanofiltration. Alternatively, or in addition, electrodialysis may also be used to concentrate the charged ido-BR1. These methods use membranes of pore sizes that allow only molecules below a certain size to pass or rely on charges on the molecules to allow or not allow them to pass through the membrane. Anion and cation exchange resins may also be used to concentrate the ido-BR1.

When isolated from a natural source, the compound for use according to the invention may be purified. In embodiments where the compound is formulated together with a pharmaceutically acceptable excipient, any suitable excipient may be used, including for example inert diluents, disintegrating agents, binding agents, lubricating agents, sweetening agents, flavouring agents, colouring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc.

The pharmaceutical compositions may take any suitable form, and include for example tablets, elixirs, capsules, solutions, suspensions, powders, granules and aerosols.

The pharmaceutical composition may take the form of a kit of parts, which kit may comprise the composition of the invention together with instructions for use and/or a plurality of different components in unit dosage form.

Tablets for oral use may include the compound for use according to the invention, mixed with pharmaceutically acceptable excipients, such as inert diluents, disintegrating agents, binding agents, lubricating agents, sweetening agents, flavouring agents, colouring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract. Capsules for oral use include hard gelatin capsules in which the compound for use according to the invention is mixed with a solid diluent, and soft gelatin capsules wherein the active ingredient is mixed with water or an oil such as peanut oil, liquid paraffin or olive oil.

Formulations for rectal administration may be presented as a suppository with a suitable base comprising for example cocoa butter or a salicylate. Formulations suitable for vaginal administration may be presented as pessaries, tampons, creams, gels, pastes, foams or spray formulations containing in addition to the active ingredient such carriers as are known in the art to be appropriate.

For intramuscular, intraperitoneal, subcutaneous and intravenous use, the compounds of the invention will generally be provided in sterile aqueous solutions or suspensions, buffered to an appropriate pH and isotonicity. Suitable aqueous vehicles include Ringer's solution and isotonic sodium chloride. Aqueous suspensions according to the invention may include suspending agents such as cellulose derivatives, sodium alginate, polyvinylpyrrolidone and gum tragacanth, and a wetting agent such as lecithin. Suitable preservatives for aqueous suspensions include ethyl and n-propyl p-hydroxybenzoate.

The compounds of the invention may also be presented as liposome formulations.

For oral administration the compound can be formulated into solid or liquid preparations such as capsules, pills, tablets, troches, lozenges, melts, powders, granules, solutions, suspensions, dispersions or emulsions (which solutions, suspensions dispersions or emulsions may be aqueous or non-aqueous). The solid unit dosage forms can be a capsule which can be of the ordinary hard- or soft-shelled gelatin type containing, for example, surfactants, lubricants, and inert fillers such as lactose, sucrose, calcium phosphate, and cornstarch.

In another embodiment, the compounds of the invention are tableted with conventional tablet bases such as lactose, sucrose, and cornstarch in combination with binders such as acacia, cornstarch, or gelatin, disintegrating agents intended to assist the break-up and dissolution of the tablet following administration such as potato starch, alginic acid, corn starch, and guar gum, lubricants intended to improve the flow of tablet granulations and to prevent the adhesion of tablet material to the surfaces of the tablet dies and punches, for example, talc, stearic acid, or magnesium, calcium, or zinc stearate, dyes, colouring agents, and flavouring agents intended to enhance the aesthetic qualities of the tablets and make them more acceptable to the patient.

Suitable excipients for use in oral liquid dosage forms include diluents such as water and alcohols, for example, ethanol, benzyl alcohol, and the polyethylene alcohols, either with or without the addition of a pharmaceutically acceptably surfactant, suspending agent or emulsifying agent.

The compounds of the invention may also be administered parenterally, that is, subcutaneously, intravenously, intramuscularly, or interperitoneally.

In such embodiments, the compound is provided as injectable doses in a physiologically acceptable diluent together with a pharmaceutical carrier (which can be a sterile liquid or mixture of liquids). Suitable liquids include water, saline, aqueous dextrose and related sugar solutions, an alcohol (such as ethanol, isopropanol, or hexadecyl alcohol), glycols (such as propylene glycol or polyethylene glycol), glycerol ketals (such as 2,2-dimethyl-1,3-dioxolane-4-methanol), ethers (such as poly(ethylene-glycol) 400), an oil, a fatty acid, a fatty acid ester or glyceride, or an acetylated fatty acid glyceride with or without the addition of a pharmaceutically acceptable surfactant (such as a soap or a detergent), suspending agent (such as pectin, carhomers, methylcellulose, hydroxypropylmethylcellulose, or carboxymethylcellulose), or emulsifying agent and other pharmaceutically adjuvants. Suitable oils which can be used in the parenteral formulations of this invention are those of petroleum, animal, vegetable, or synthetic origin, for example, peanut oil, soybean oil, sesame oil, cottonseed oil, corn oil, olive oil, petrolatum, and mineral oil. Suitable fatty acids include oleic acid, stearic acid, and isostearic acid. Suitable fatty acid esters are, for example, ethyl oleate and isopropyl myristate.

Suitable soaps include fatty alkali metal, ammonium, and triethanolamine salts and suitable detergents include cationic detergents, for example, dimethyl dialkyl ammonium halides, alkyl pyridinium halides, and alkylamines acetates; anionic detergents, for example, alkyl, aryl, and olefin sulphonates, alkyl, olefin, ether, and monoglyceride sulphates, and sulphosuccinates; nonionic detergents, for example, fatty amine oxides, fatty acid alkanolamides, and polyoxyethylenepolypropylene copolymers; and amphoteric detergents, for example, alkyl-beta-aminopropionates, and 2-alkylimidazoline quarternary ammonium salts, as well as mixtures.

The parenteral compositions of this invention will typically contain from about 0.5 to about 25% by weight of the compound for use according to the invention in solution. Preservatives and buffers may also be used. In order to minimize or eliminate irritation at the site of injection, such compositions may contain a non-ionic surfactant having a hydrophile-lipophile balance (HLB) of from about 12 to about 17. The quantity of surfactant in such formulations ranges from about 5 to about 15% by weight. The surfactant can be a single component having the above HLB or can be a mixture of two or more components having the desired HLB. Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The compound for use according to the invention may also be administered topically, and when done so the carrier may suitably comprise a solution, ointment or gel base. The base, for example, may comprise one or more of the following: petrolatum, lanolin, polyethylene glycols, bee wax, mineral oil, diluents such as water and alcohol, and emulsifiers and stabilizers. Topical formulations may contain a concentration of the compound from about 0.1 to about 10% w/v (weight per unit volume).

When used adjunctively, the compound for use according to the invention may be formulated for use with one or more other drug(s). Thus, adjunctive use may be reflected in a specific unit dosage designed to be compatible (or to synergize) with the other drug(s), or in formulations in which the compound is admixed with one or more enzymes. Adjunctive uses may also be reflected in the composition of the pharmaceutical kits of the invention, in which the compounds of the invention is co-packaged (e.g. as part of an array of unit doses) with the enzymes. Adjunctive use may also be reflected in information and/or instructions relating to the co-administration of the compound and/or enzyme.

Cosmetic Formulations

The cosmetic compositions of the invention may be selected for example from moisturizing compositions, cleansing compositions, or any composition that may provide a benefit to the skin. The cosmetic compositions of the invention may comprise cosmetically-acceptable excipients or carriers, for example selected from those described below.

In one embodiment, the cosmetic composition is a cleansing composition. Suitable cleansing compositions are solid or semi-solid at room temperature. Examples of useful cleansing compositions include, but are not limited to, fatty acid soaps, including glycerin soaps, synthetic detergents and mixtures thereof. Solid cleansing compositions are extensively taught in Soap Technology for the 1990's, the contents of which are incorporated herein by reference. It is desirable that the cleansing composition be flowable.

In one embodiment of the invention, the cleansing composition comprises glycerin soap. Examples of glycerin soaps useful in the present invention include but are not limited to those disclosed in U.S. Pat. Nos. 4,405,492 and 4,879,063, the disclosures of which are hereby incorporated by reference.

Examples of suitable fatty acid soaps include soaps derived from hydrocarbon chain lengths of from approximately 10 to 22 (including carboxyl carbon) and may be saturated or unsaturated. The soap may be, for example, the sodium salt, potassium salt, ammonium salt, triethanolammonium salt and mixtures thereof.

Suitable synthetic detergents include those known in the art for the desired purpose. Examples of detergents useful for personal cleansing include the isethionates, sarcosinates, and glyceryl ether sulfonates which may be pure chain length variants or those derived from commercial oils such as coconut oil. Other suitable detergents include anionic acyl sarcosinates, methyl acyl taurates, N-acyl glutamates, alkyl sulphosuccinates, alkyl phosphate esters, ethoxylated alkyl phosphate esters, trideceth sulphates, protein condensates, mixtures of ethoxylated alkyl sulphates and alkyl amine oxides, betaines, sultaines and mixtures thereof. Included are the alkyl ether sulphates with 1 to 12 ethoxy groups, especially ammonium and sodium lauryl ether sulphates.

The cosmetic composition may be a moisturizing composition.

Other optional components of the cosmetic compositions of the invention include, but are not limited to, perfumes, fragrances, preservatives, colourants, dyes, anti-caking agents, and personal care ingredients, including, but are not limited to, skin and hair care ingredients.

Examples of suitable personal care ingredients useful in the present invention include but are not limited to safe and effective amounts of: humectants, sunscreen actives, skin soothers, anti-irritants, anti-inflammatories, emollients, conditioning agents, moisturizers, deodorants, anti-perspirants, artificial tanning agents, antimicrobial agents, anti-acne agents, anti-wrinkle agents, anti-skin atrophy agents, skin firming agents, anti-itch agents, anti-fungal agents, topical anaesthetics, skin tone evening agents, active natural ingredients, agents for minimizing the appearance or retarding regrowth of unwanted hair, skin texture modifiers, and additional cleansing agents.

In one embodiment the ido-BR1 may be used from a water or alcoholic water extract by using a water in oil (w/o) emulsion such as are employed for example in the treatment of dry skin and emollient applications Emollients function by their ability to remain on the skin surface or in the stratum corneum to act as lubricants, to reduce flaking, and to improve the skin appearance. Typical emollients include fatty esters, fatty alcohols, mineral oil, polyether siloxane copolymers and the like. Examples of suitable emollients include, but are not limited to, polypropylene glycol ("PPG")-15 stearyl ether, PPG-10 cetyl ether, steareth-10, oleth-8, PPG-4 lauryl ether, vitamin E acetate, PEG-7 glyceryl cocoate, lanolin, and combinations thereof. Vitamin E acetate, PEG-7 glyceryl cocoate and combinations thereof are preferred.

Examples of suitable humectants include polyhydric alcohols. Suitable polyhydric alcohols include, but are not limited to, glycerol (also known as glycerin), polyalkylene glycols, alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-dibutylene glycol, 1,2,6,-hexanetriol, ethoxylated glycerol, propoxylated glycerol and mixtures thereof.

Suitable skin soothers include, but are not limited to, panthenol, bisabolol, allantoin, aloe, and combinations thereof.

Suitable conditioning agents include, but are not limited to, dimethicone propyl PG-betaine, dimethicone copolyols, polyquaternium-10, guar, guar derivatives, and combinations thereof. Suitable anti-acne active ingredients include, but are not limited to, salicylic acid, sulphur, lactic acid, glycolic acid, pyruvic acid, urea, resorcinol, N-acetylcysteine, retinoic acid, benzoyl peroxide, octopirox, triclosan, azelaic acid, phenoxyethanol, phenoxypropanol, flavinoids, derivatives thereof, and combinations thereof. Salicylic acid and benzoyl peroxide are preferred.

EXEMPLIFICATION

The invention will now be described with reference to specific Examples. These are merely exemplary and for illustrative purposes only: they are not intended to be limiting in any way to the scope of the monopoly claimed or to the invention described. These examples constitute the best mode currently contemplated for practicing the invention.

Example 1

Identification of ido-BR1 in Cucumber

Extraction of cucumber fruits in water or aqueous solvents such as 70% aq. ethanol is effective at extracting the ido-BR1. Cation exchange resins such as IR120 or Dowex 50 resin in the H$^+$ form (or similar form selected by those practiced in the art) will provide a concentrated fraction containing ido-BR1 along with amino acids. Use of an anion exchange resin such as CG400 or Dowex 1 in the OH$^-$ form (or similar form selected by those practiced in the art) will also provide an ido-BR1-enriched fraction.

GC-MS

All samples from ion exchange columns were freeze dried before derivatization. Trimethylsilyl (TMS) derivatives were prepared using a mixture of hexamethyldisilazane and trimethylchlorosilane in pyridine (Pierce 'Tri-Sir' silylation reagent, HMDS:TMCS:pyridine in a ratio of 2:1:10). Samples were heated at 60° C. for 15 minutes and then left at room temperature for at least 60 min. Insoluble reaction products were sedimented by centrifugation, and the supernatant was transferred to fresh vials using a syringe.

Analysis was carried out by GC-MS using a Perkin Elmer Autosystem XL gas chromatograph with a high polarity fused-silica column (Varian 'Factor Four' VF-5ms column, 25 m×0.25 mm i.d., 0.25 μm phase thickness). The carrier gas (helium) flow rate was 1 ml min-1. Trimethylsilyl— (TMS) derivatives were separated using a temperature programme that started at 160° C. for 5 min, followed by a linear increase to 300° C. at a rate of 10° C. min-1. Electron impact mass spectrometry of the column eluant was carried out using a Perkin Elmer TurboMass Gold mass spectrometer, with a quadrupole ion filter system, which was run at 250° C. constantly during analysis. The injection volume was 1 μl.

Ido-BR1 gives a distinctive mass spectrum as the trimethylsilyl-derivative with major fragments seen at 147, 217, 258, 330 and 420 amu. It is clearly distinguishable in cucumber extract at concentrations comparable to the primary amino acids such as aspartic acid. Using the GC method described ido-BR1 has a retention time of 10.45 minutes with the common amino acids seen at 3-5 minutes. The retention time of ido-BR1 is comparable to that of the trimethylsilyl-derivatives of glucose. The removal of glucose by the ion exchange methods described allows the determination of ido-BR1 by GC-MS. No other iminosugars or iminosugar acids are present in cucumber fruits.

Example 2

Confirmation of the Structure of ido-BR1

Purification of the cucumber ido-BR1 is complicated by the common amino acids that are present at similar concentrations in the fruit. However, after concentration using cation and anion exchange chromatography it is possible to further purify the ido-BR1 by passing it down a neutral alumina oxide column and eluting with water to give a nearly pure compound (JH0808/155/water) that could be used for proton and carbon NMR to confirm the structure by comparison with synthetic ido-BR1.

Example 3

Glycosidase Assays

All enzymes and para-nitrophenyl substrates were purchased from Sigma, with the exception of beta-mannosidase which came from Megazyme. Enzymes were assayed at 27° C. in 0.1 M citric acid/0.2M disodium hydrogen phosphate buffers at the optimum pH for the enzyme. The incubation mixture consisted of 10 μl enzyme solution, 10 μl of 1 mg/ml aqueous solution of sample and 50 μl of the appropriate 5 mM para-nitrophenyl substrate made up in buffer at the optimum pH for the enzyme. The reactions were stopped by addition of 70 μl 0.4M glycine (pH 10.4) during the exponential phase of the reaction, which had been determined at the beginning using uninhibited assays in which water replaced inhibitor. Final absorbances were read at 405 nm using a Versamax microplate reader (Molecular Devices). Assays were carried out in triplicate, and the values given are means of the three replicates per assay. The method was carried out as described in Watson et al. (1997) Phytochemistry 46 (2): 255-259.

The table below shows the percentage inhibition caused by DNJ, BR1 and ido-BR1 when tested on a panel of glycosidases at 0.2 mM. A negative value suggests a stabilisation of the enzyme or promotion of the enzyme activity (perhaps by binding to a non-catalytic site). DNJ shows potent inhibition of glucosidases but BR1 is a poor inhibitor and ido-BR1 very weakly inhibitory to the two glucosidases it was tested on. BR1 is a good inhibitor of glucuronidase but ido-BR1 is not inhibitory. Ido-BR1 appears to promote alpha-mannosidase activity slightly. From these results we suggest that ido-BR1 will not inhibit digestive glucosidases significantly and therefore will have a better drug profile than DNJ for inflammatory disorders.

| Assay | DNJ | BR1 | 6-epi-BR1 |
|---|---|---|---|
| α-D-glucosidase (Yeast) | 35.7 | 4.9 | 4.7 |
| α-D-glucosidase (Bacillus) | 99.5 | 49.2 | 26.4 |
| α-D-glucosidase (Rice) | 99.6 | 55.2 | — |
| β-D-glucosidase | 63.7 | 6.7 | 6.1 |
| α-D-galactosidase | −3.3 | −6.3 | −2.7 |
| β-D-galactosidase | 0.4 | 6.2 | 1.0 |
| α-L-fucosidase | 5.9 | 1.6 | — |
| α-D-mannosidase | 26.6 | 28.9 | −28.4 |
| β-D-mannosidase | −19.0 | 7.8 | −4.4 |
| Naringinase | 20.8 | 1.4 | — |
| N-acetyl-β-D-gluc (Bovine kidney) | −0.8 | 2.4 | 5.5 |
| N-acetyl-β-D-gluc (Jack bean) | 2.8 | 10.4 | −4.5 |
| N-acetyl-β-D-hexosaminidase | −5.5 | −1.1 | — |
| Amyloglucosidase | 31.7 | 5.5 | — |
| β-glucuronidase | — | 88.9 | 2.5 |

Example 4

Ido-BR1 Abrogates Inflammation 24 H after Challenge in an In Vitro Model

The efficacy of ido-BR1 as an anti-inflammatory agent in a model of mucosal inflammation was tested. The model utilised was previously optimised and established (D M Nash, E A. Lane, S Herath and I M Sheldon (2008) Endometrial Explant Culture for Characterizing Equine Endometritis. American Journal of Reproductive Immunology. 59: 105-117). The model is comprised of an in vitro equine endometrial explant tissue culture system. There are several advantages of using uterine tissue collected from horses: large uterine surface area to harvest copious tissue enabling several treatments and replicates in a single experiment (ensures statistical robustness); directly representative of whole animal clinical inflammation in the horse (uterine inflammation is a significant cause of subfertility), and indirectly of other species (e.g. cattle and humans) and inflammation at other mucosal surfaces (e.g. gut and lung).

Uterine tissue was collected from mares at an abattoir, the endometrial (mucosal) surface was dissected out, homogenised and placed in culture as explants. In order to stimulate inflammation synonymous to that which occurs with natural uterine infection in the whole animal, the O-antigen of *E. coli*, lipopolysaccharide (LPS), was added to the cultured explants. Inflammation was indicated by measuring the secretion of an established marker of inflammation, Prostaglandin $F_{2\alpha}$ ($PGF_{2\alpha}$), by explants from the culture media. The secretion of $PGF_{2\alpha}$ is measured at 24 and 72 h after challenge with LPS in order to represent the innate and chronic immune response respectively.

Explants were treated with control (media alone) or, in order to determine whether ido-BR1 affected spontaneous $PGF_{2\alpha}$, 0.5, 25 or 100 μg/ml ido-BR1 alone. In order to test the ability of ido-BR1 to abrogate the inflammatory response, explants were treated with 3.0 μg/ml LPS alone, or 3.0 μg/ml LPS in the presence of 0.5, 25 or 100 μg/ml ido-BR1. The secretion of $PGF_{2\alpha}$ was measured at 24 and 72 h after treatments were applied. Explants were collected from 4 different animals (n=4) and each treatment was conducted using explants cultured in triplicate for each animal.

Twenty four hours after treatment, explants that were exposed to the ido-BR1 alone (without LPS), secreted $PGF_{2\alpha}$ concentrations that were similar (not significantly different) to the control. Therefore, the ido-BR1 itself did not inadvertently stimulate inflammation in the explants. Explants treated with LPS alone secreted $PGF_{2\alpha}$ concentrations that were significantly greater than that of the control, indicating inflammation was stimulated by LPS. Explants that were treated with LPS and ido-BR1 concurrently secreted $PGF_{2\alpha}$ concentrations that were not significantly different to the control.

Therefore, the ido-BR1 abrogated inflammation in the explants. The abrogation of inflammation by ido-BR1 occurred in a dose-dependent manor. However, the effect, although showing a similar pattern, was not significant at 72 h.

EQUIVALENTS

The foregoing description details presently preferred embodiments of the present invention. Numerous modifications and variations in practice thereof are expected to occur to those skilled in the art upon consideration of these descriptions. Those modifications and variations are intended to be encompassed within the claims appended hereto.

The invention claimed is:

1. A method for treating an inflammatory disease comprising administering an effective amount of a composition comprising (2R,3R,4R,5S)-3,4,5-trihydroxypiperidine-2-carboxylic acid, or a pharmaceutically acceptable salt thereof, and a pharmaceutically-acceptable excipient or carrier, to a subject in need thereof.

2. The method of claim 1, wherein the inflammatory disease is an autoimmune disease.

3. The method of claim 2, wherein the autoimmune disease is ulcerative colitis.

4. The method of claim 2, wherein the autoimmune disease is inflammatory bowel disease.

5. The method of claim 2, wherein the autoimmune disease is rheumatoid arthritis.

6. The method of claim 1, wherein the inflammatory disease is psoriatic arthritis.

7. The method of claim 1, wherein the inflammatory disease is enteropathic arthritis.

8. The method of claim 1, wherein the inflammatory disease is reactive arthritis.

9. The method of claim 1, wherein the inflammatory disease is arthritis associated with inflammatory bowel disease.

10. The method of claim 1, wherein the (2R,3R,4R,5S)-3,4,5-trihydroxypiperidine-2-carboxylic acid, or pharmaceutically acceptable salt thereof, is present in the composition at a level of about 1% w/w to about 50% w/w (on a dry weight basis).

11. The method of claim 1, wherein the (2R,3R,4R,5S)-3,4,5-trihydroxypiperidine-2-carboxylic acid, or pharmaceutically acceptable salt thereof, is present in the composition at a level of about 50% w/w to about 99% w/w (on a dry weight basis).

12. The method of claim 1, wherein the (2R,3R,4R,5S)-3,4,5-trihydroxypiperidine-2-carboxylic acid, or pharmaceutically acceptable salt thereof, is present in the composition at a level of up to 1% w/w (on a dry weight basis).

13. The method of claim 1, wherein the (2R,3R,4R,5S)-3,4,5-trihydroxypiperidine-2-carboxylic acid, or pharmaceutically acceptable salt thereof, is present in the composition at a level of up to 5% w/w (on a dry weight basis).

14. The method of claim 1, wherein the (2R,3R,4R,5S)-3,4,5-trihydroxypiperidine-2-carboxylic acid, or pharmaceutically acceptable salt thereof, is present in the composition at a purity level of at least 90% w/w.

15. The method of claim 1, wherein the (2R,3R,4R,5S)-3,4,5-trihydroxypiperidine-2-carboxylic acid, or pharmaceutically acceptable salt thereof, is administered topically.

16. The method of claim 1, wherein the (2R,3R,4R,5S)-3,4,5-trihydroxypiperidine-2-carboxylic acid, or pharmaceutically acceptable salt thereof, is orally administered.

17. The method of claim 1, wherein the (2R,3R,4R,5S)-3,4,5-trihydroxypiperidine-2-carboxylic acid, or pharmaceutically acceptable salt thereof, is parenterally administered.

18. The method of claim 1, wherein the (2R,3R,4R,5S)-3,4,5-trihydroxypiperidine-2-carboxylic acid, or pharmaceutically acceptable salt thereof, is administered by buccal or sublingual application.

19. The method of claim 1, further comprising administering an anti-inflammatory agent.

20. The method of claim 19, wherein the effective amount is about 0.1 mg/kg to about 50 mg/kg of (2R,3R,4R,5S)-3,4,5-trihydroxypiperidine-2-carboxylic acid, or pharmaceutically acceptable salt thereof, administered daily.

* * * * *